US005643942A

United States Patent [19]
Hester, Jr. et al.

[11] Patent Number: 5,643,942

[45] Date of Patent: Jul. 1, 1997

[54] METHODS, COMPOSITION AND SOLUTIONS FOR TREATING ALOPECIA

[75] Inventors: Jackson B. Hester, Jr., Galesburg; Kaushik D. Meisheri, Kalamazoo, both of Mich.

[73] Assignee: The Upjohn Company, Kalamazoo, Mich.

[21] Appl. No.: 180,001

[22] Filed: Jan. 11, 1994

Related U.S. Application Data

[63] Continuation of Ser. No. 857,715, Mar. 25, 1992, abandoned, which is a continuation of Ser. No. 675,032, Mar. 25, 1991, abandoned, which is a continuation of Ser. No. 499,574, Mar. 26, 1990, abandoned, which is a continuation of Ser. No. 312,773, Feb. 7, 1989, abandoned, which is a continuation of PCT/US87/01496, Jun. 30, 1987, which is a continuation of Ser. No. 894,969, Aug. 8, 1986, abandoned.

[51] Int. Cl.$^6$ ........................................... A61K 31/35
[52] U.S. Cl. .......................... 514/456; 514/422; 514/880
[58] Field of Search ................................. 514/320, 880, 514/456

[56] References Cited

U.S. PATENT DOCUMENTS

| 4,139,619 | 2/1979 | Chidsey, III | 424/45 |
| 4,311,707 | 1/1982 | Birnbaum et al. | 424/305 |
| 4,431,833 | 2/1984 | Lodhi et al. | 560/2 |
| 4,446,113 | 5/1984 | Evans | 424/267 |
| 4,596,812 | 6/1986 | Chidsey, III et al. | 514/256 |
| B1 4,446,113 | 12/1985 | Evans et al. | |

OTHER PUBLICATIONS

B1 4,446,113 Dec. 1985 Ryans et al. Re–Examination Certificate Current Therapy, 1984, pp. 559–603.

*Primary Examiner*—Shelley A. Dodson
*Attorney, Agent, or Firm*—William G. Jameson

[57] ABSTRACT

This invention relates to the method for treating the form of alopecia commonly known as "male pattern baldness" which comprises regular topical application to the affected areas of the human scalp of a composition containing as at least one of its active ingredients of Formula I. It also encompasses the aforesaid compound itself for use as a therapeutic agent to arrest and reverse male pattern alopecia.

13 Claims, No Drawings

METHODS, COMPOSITION AND SOLUTIONS FOR TREATING ALOPECIA

This application is a continuation of U.S. Ser. No. 07/857,715, filed 25 Mar. 1992, now abandoned; which is a continuation of U.S. Ser. No. 07/675,032, filed 25 Mar. 1991, abandoned; which is a continuation of U.S. Ser. No. 07/499,574, filed 26 Mar. 1990, abandoned; which is a continuation of 07/312,773, filed 7 Feb. 1989, abandoned; which is a continuation of International Patent Application No. PCT/US87/01496, filed 30 Jun. 1987; which is a continuation of U.S. Ser. No. 06/894,969, filed 8 August 1986, abandoned.

BACKGROUND OF SUMMARY

The present invention relates to methods. compositions and solutions for treating human alopecia, including male pattern alopecia (androgenic alopecia) and alopecia areata, involving the use of a substance known as BRL-34915 and related 4-amino and 4-amido-substituted chromans, chromenes, and chromanols of Formula I, in association with a pharmaceutical carrier adapted for topical application.

European Patent Publication Nos. 76075, 91748, 93535, 95316, 107423, 120426, 120427, 126311, 126350, 126367, 138134 and 173848 describe classes of chromanols, chromenes and chromans having antihypertensive activity and that they are of potential use in the treatment of other cardiovascular disorders. Such disorders include congestive heart failure, engine, peripheral vascular disease and cerebral vascular disease.

Dermatologists recognize many different types of hair loss, the most common by far being "androgenic alopecia" wherein human males begin losing scalp hair at the temples and on the crown of the head as they get older while this type of hair loss is largely confined to males, hence its common name "male pattern baldness", it is not unknown in women.

Dr. Charles A. Chidsey, III and Dr. Guinter Kahn disclose and claim in U.S. Pat. No. 4,596,812 the use of minoxidil, 6-amino-1,2-dihydro-1-hydroxy-2-imino-4-piperidinopyrimidine, as a therapeutic agent to treat alopecia and arrest and reverse male pattern alopecia. See also U.S. Pat. No. 4,139,619 which claims the use of minoxidil and related 6-amino-4-(substituted amino)-1,2-dihydro-1-hydroxy-2-iminopyrimidines as a means for (a) increasing the rate of growth of terminal hair, and (b) converting vellus hair to growth as terminal hair.

The use of retinoids alone or in combination with minoxidil and related substituted pyrimidines to increase the rate of hair growth is disclosed in PGT publication numbers US85/04577, PGT US83/02558 and PCT US82/02833.

The use of minoxidil sulphate (2,6,-diamino-4-(1-piperidinyl)-1-(sulfooxy)-pyrimidinium hydroxide inner salt) as therapeutic agent to stimulate the rate of hair growth is disclosed in PCT Application US86/00073, filed 23 Jan. 1986. In addition, the induced relaxation of rabbit superior mesenteric artery smooth muscle by minoxidil sulphate and dependence on potassium permeability has been reported. See K. D. Meisheri, et al, "The Mechanisms of Vascular Smooth Muscle Relaxing Effects of Minoxidil Sulfate"; Smooth Muscle Function Symposium Proceedings: Official Satellite Symposium of the XXX Internation Congress of the International Union of Physiological Sciences, Banff Center, Banff, Canada, 1986, page 114, abstract W4-P5.

Notwithstanding the fact that nothing before the use of topical application of minoxidil had been found which was effective in preventing, let alone reversing, male pattern baldness, a good deal is known about various types of human hair and its growth patterns on various parts of the body.

For purposes of the present invention, we need only consider two types of hair, namely "terminal hairs" and "vellus hairs". Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, (1) the anagen phase (2) the catagen phase and (3) the telogen phase. The anagen phase is the period of active hair growth and, insofar as scalp hair is concerned, this generally lasts from 3–5 years. The catagen phase is a short transitional phase between the anagen and telogen phases which, in the case of scalp hair, lasts only 1–2 weeks. The final phase is the telogen phase which, for all practical purposes, can be denominated by a "resting phase" where all growth ceases and the hair eventually is shed preparatory to the follicle commencing to grow a new one. Scalp hair in the telogen phase is also relatively short-lived, some 3–4 months elapsing before the hair is shed and a new one beings to grow.

Now, under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

The remaining result associated with alopecia is the severe diminution of hair follicles. A bald human subject will average only about 306 follicles per square centimeter, whereas, a non-bald one in the same age group (30–90 years) will still have an average of 460 follicles per square centimeter. This amounts to a one-third reduction in hair follicles which, when added to the increased proportion of vellus hair follicles and the increase number of hair follicles in telogen, is both significant and noticeable. It is written that approximately 50% of the hairs must be shed to produce visible thinning of scalp hair. It is thus a combination of these factors: (1) transition of hairs from terminal to vellus, (2) increased number of telogen hairs—some of which have been shed, and (3) loss of hair follicles (atrophy in Settel's description) that produces "baldness".

Now, while a good deal is known about the results of male pattern baldness, very little is known about its cause. About all that can be said is that the cause is felt to be genetic and hormonal in origin although as will be seen presently, the known prior art attempts to control it through hormone adjustment have been singularly unsuccessful.

At the present time, one known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Furthermore, the solution is inadequate from the standpoint that it becomes a practical, if not an economic, impossibility to replace but a tiny fraction of the hair present in a normal healthy head of hair.

As far as the other non-drug related approaches to the problem are concerned, they include such things as ultraviolet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were uniformly disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have been even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm being about maximum. Once the patient ceases taking the drug, the hair reverts to whatever is normal for the particular site after six months to a year has elapsed. An example of such a drug is diphenylhydantoin which is an anticonvulsant drug widely used to control epileptic seizures. Hypertrichosis is frequently observed in epileptic children some two or three months after starting the drug and first becomes noticeable on the extensor aspects of the limbs and later on the trunk and face. The pattern is not unlike that sometimes caused by injury to the head. As for the hair, it is often shed when the drug is discontinued but may, in some circumstances, remain.

"Minoxidil", as was true with "Diazoxide", produced a good deal of hypertrichosis in patients to whom the drug was administered. See, for example, Journal of Laboratory and Clinical Medicine, Vol, 79, page 639, April, 1972; Circulation, Vol. 45. page 571, March 1972; and Clinical Pharmacy and Therapy, Vol. 13, page 436, 1972.

Streptomycin is another drug that has been found to produce hypertrichosis in much the same way as diphenylhydantoin when administered to children suffering from tuberculous meningitis. About the same effects were observed and the onset and reversal of the hypertrichosis in relation to the period of treatment with the antibiotic leave little, question but that it was the causative agent.

The compounds of the subject invention (Formula I) including, namely, 6-cyano-3,4-dihydro-2,2-dimethyl-trans-4-(2-oxo-1-pyrrolidinyl)-2H-benzo[b]pyran-3-ol and trans-4-N-acetyl-ethylamino-6-cyano-3,4-dihydro-2,2-dimethyl-2H-benzo[b]pyran-3-ol, are far different from diazoxide, and the 6-amino-4-(substituted amino)-1,2-dihydro-1-hydroxy-2-iminopyrimidines of U.S. Pat. No. 4,139,619 and 4,596,812.

The compound 6-cyano-3,4-dihydro-2,2-dimethyl-trans-4-(2-oxo-1-pyrrolidinyl)-2H-benzo[b]pyran-3-ol, hereinafter to be referred to by the coined term "BRL-34915", was disclosed by J. M. Evans, R. E. Buckingham and K. Willcocks and it forms the subject matter among other similar compounds of U.S. Pat. No. 4,446,113 issued May 1, 1984. See Example 1 of U.S. Pat. 4,446,113. This compound, among others of Formula I, has been reported as a potent vasodilator anti-hypertensive agent and is currently under preclinical evaluation. It is a so-called direct acting "vasodilator" which, as the name implies, functions to dilate the peripheral vascular system. It is reported to act in a novel manner for an anti-hypertensive agent to cause hyperpolarisation of the cell membrane by activation of the outward conductance of potassium ions. The cell membrane is desensitized and the inward. movement of calcium is reduced in a way different from that of the calcium antagonist nifedipine See e.g., Br. J. Pharmac. (1986), 88, 121–128 and Br. J. Pharmac. (1986), 88, 103–111. It has not been reported to produce hypertrichosis so far as applicants are aware.

Minoxidil is a known vasodilator. Following reports of the use of minoxidil and related compounds to stimulate hair growth, and as a treatment of male pattern alopecia, other vasodilators including "viprostol" and "diazoxide" are reported as being evaluated by others to stimulate hair growth. See for example U.S. Pat. Nos. 4,431,833 and 4,311,707; European Patent 027,665 (published 04/29/81).

Vasodilators as a general class of therapeutic agents have, so far as applicants are aware, never proven effective to grow hair on the scalp as a result of topical application thereof to bald areas.

It is, therefore, the principal object of the present invention to provide a novel, unobvious and effective treatment for male pattern baldness.

Another object of the invention forming the subject matter hereof is to provide a method of treating certain types of baldness in humans that is compatible with various types of therapeutic agents or carriers and, therefore, would appear to be combinable with those which, by themselves. demonstrates some therapeutic activity such as, for example, microemulsion creams containing estradiol and oxandrolone.

Still another objective is the provision of a treatment for alopecia which, while effective for its intended purpose, is apparently non-toxic and relatively free of unwanted side effects.

An additional object of the invention herein disclosed and claimed is to provide a method for treating baldness in men which comprises application of a compound of Formula I by the patient himself under medical supervision no more stringent than that demanded for other topically-administered therapeutic agents.

Other objects of the invention are to provide a treatment for male pattern alopecia which is safe, simple, painless, cosmetic in the sense of being invisible, easy to apply and quite inexpensive when compared with hair transplanted and the like.

Further objects will be in part apparent and in part pointed out specifical hereinafter in connection with the detailed description of the invention which follows.

Dermatologists and others were well aware of the fact that prolonged vasodilation of certain areas of the human body other than the scalp sometimes resulted in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by mental retardates and localized stimulation of the shoulders by water carriers has been noted to bring on hypertrichosis in the affected areas. Be that as it may, similar techniques such as continued periodic massage of the scalp have been found totally ineffective as a means for restoring lost hair growth to the scalp. Scar tissue on the scalp inhibits rather than promotes hair growth.

DETAILED DESCRIPTION

This invention relates to the method for treating alopecia, including androgenic alopecia (male pattern baldness male pattern alopecia) and alopecia areata, which comprises regular topical application to the affected areas of the human skin a pharmaceutical composition containing as at least one of its active ingredients a compound of Formula I. It also encompasses the use of a compound of Formula I as a therapeutic agent to arrest and reverse androgenic alopecia.

The compounds of this invention are represented by Formula I wherein either one of $R_1$ and $R_2$ is hydrogen and the other is selected from the class of $C_{1-6}$ alkylcarbonyl, $C_{1-6}$ alkoxycarbonyl, $C_{1-6}$alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$alkoxycarbonylamino, $C_{1-6}$ alkyl-thiocarbonyl, $C_{1-6}$ alkoxythiocarbonyl, $C_{1-6}$ alkylthiocarbonyloxy, $C_{1-6}$ alkoxythiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphinylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl; aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups;

$R_8$ is hydrogen or $C_{1-6}$ alkyl; or $R_7$ and $R_8$ are joined together to form $C_{3-5}$ polymethylene or —CH$_2$—(CH$_2$)n—Z—(CH$_2$)m— where m and n are integers 0 to 2 such that m+n is 1 or 2 and Z is oxygen, sulphur or NR$_9$ wherein $R_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen; mono- or bi-cyclic heteroarylcarbonyll X is oxygen or sulphur and the R$_8$NCXR$_7$ moiety is trans to the R$_5$ group when R$_5$ is hydroxy, $C_{1-6}$ alkoxy or $C_{1-7}$ acyloxy; or a pharmaceutically acceptable salt or solvate thereof.

Examples of $R_7$ aryl include phenyl and naphthyl.

Examples of $R_7$ heteroaryl include 5- or 6-membered monocyclic or 9- or 10-membered bicyclic heteroaryl. In addition, 5- or 6-membered monocyclic or 9- or 10-membered bicyclic heteroaryl can be optionally contain one, two or three heteroatom which are selected from the class of oxygen, nitrogen and sulphur and which, in the case of there being more than one heteroatom, are the same or different.

Suitable values for $R_8$, when $R_7$ and $R_8$ are not joined together include hydrogen, methyl, ethyl, n- and iso-propyl, n-, sec- and tert-butyl.

Examples of 5- or 6-membered monocyclic heteroaryl containing one, two or three heteroatoms which are selected from the class of oxygen, nitrogen and sulphur include furanyl, thienyl, pyrryl, oxazolyl, thiazolyl, imidazolyl and thiadiazolyl, and pyridinyl, pyridazinyl, pyrimidinyl, pyrazinyl and triazinyl. Preferred examples of such groups include furanyl, thienyl, pyrryl and pyridyl, in particular 2-and 3-furanyl, 2- and 4-pyrryl, 2- and 3-thienyl, and 2-, 3- and 4-pyridinyl.

Examples of 9- or 10-membered bicyclic heteroaryl containing one, two or three heteroatoms which are selected from the class of oxygen, nitrogen and sulphur include benzofuranyl, benzothiophenyl, indolyl and indazolyl, quinolinyl and isoquinolinyl, and quinazoninyl.

Examples of the groups or atoms for optional substitution or aryl or heteroaryl include methyl, methoxy, hydroxy, chloro, nitro or cyano.

Examples of a pharmaceutically acceptable salt of a compound of formula (I) include the acid addition salts of a compound of formula (I), wherein one or other of $R_1$ and $R_2$ is amino or an amino-containing group, for example the hydrochloride and hydrobromide salts.

Examples of a pharmaceutically acceptable solvate of a compound of formula (I) include the hydrate.

The compounds of formula (I), wherein $R_5$ is hydrogen, hydroxy, $C_{1-6}$ alkoxy or $C_{1-7}$ acyloxy and $R_6$ is hydrogen, are asymmetric and, therefore, can exist in the form of optical isomers. The present. invention extends to all such isomers individually and as mixtures, including racemic modifications.

The compounds of Formula I and methods for their preparation are disclosed in U.S. Pat. Nos. 4,446,113, 4,481, 214, 4,496,565 and 4,510,152 and allowed U.S. Ser. Nos. 482,628 (now U.S. Pat. No. 4,542,149) and 592,117 (now U.S. Pat. No. 4,555,509). (The subject matter of which are all expressly incorporated herein by reference), or by analogous methods thereto. See also J. Med. Chem. 27, 1127–1131 (1984), J. Med. Chem. 26, 1582–1589 (1983) and European Patent Application No. 173,848, published 03/12/86.

Examples of the compounds of Formula I include the examples described in the aforementioned U.S. patents as well as the aforementioned European patent applications.

A class of compounds within Formula I are those of Formula II, wherein P is 1 or 2 and the remaining variables are as defined in Formula I. The compounds of Formula II can be used in the same manner as the compounds of formula I.

The pharmaceutical compositions contemplated by this invention include pharmaceutical compositions adapted for topical application to the human scalp. Conventional pharmaceutical forms for this purpose include ointments, lotions, pastes, jellies, gels, mousses, sprays. foams, aerosols, and the like. The term "ointment" embraces formulations (including creams) having oleaginous, absorption, watersoluble and emulsion-type bases, e.g., petrolatum, lanolin, polyethylene glycols, as well as mixtures of these. The compounds may also be formulated into conventional liposomal preparations or dissolved in conventional solvents such as acetonitrile: dimethylformamide (DMF), dimethylacetamide (DMA), alcohol, propanol, and the like.

The percentage by weight of the compound of the formula I herein utilized ranges from about 0.005% to about 10.0% of the pharmaceutical preparation, preferably from about 0,05% to about 3.0% and in these preparations the aforesaid pharmaceutical carrier for topical application constitutes a major amount of the said preparation.

The pharmaceutical preparations of the subject invention are applied on a regular basis, with or without occlusion, for a period of time sufficient to effect hair growth. Occlusion of the preparation may be obtained by any conventional means such as bandages, plastic coverings, shower caps swimming cats, etc. The percentage of active ingredient (Formula I) as well as frequency of application may be varied as necessary or desirable to achieve the desired results.

Example 1

Two hundred and fifty liters of a pharmaceutically elegant 2% topical solution of BRL-34915 is prepared from:

| Propylene Glycol USP (Sp. Gr. = 1.036) | 51 kg 800 g |
| BRL-34915 (Milled) | (5 kg) 5 kg 030 g |
| Alcohol USP q.s. ad | 250 L |

The propylene glycol and 150 L. of alcohol are added to a mixing tank, the BRL-34915 is added and dissolved in the propylene glycol/alcohol mixture and additional alcohol added to make 250 liters. The resulting BRL-34915 topical solution is packaged in suitable dispensing bottles, accompanied by a metered dropper, and applied to the pre-washed scalp as a total dose of 1 ml, beginning in the center of the affected area. Twice daily application for 2 to 7 months or longer may be required before evidence of hair growth stimulation can be expected in the treatment of early, progressive male pattern baldness. Onset and degree of hair growth stimulation can be expected to vary considerably among patients.

0.1% and 1% BRL-34915 topical solutions are prepared in accordance with the foregoing procedure by utilizing 0.25 kg and 2.5 kg, respectively of BRL-34915 for the 5.0 kg utilized in the preparation of the 2% solution of Example 1.

EXAMPLE 2

Pharmaceutically elegant 0.5, 1.5 and 3% BRL-34915 gels are prepared by mixing the below-described 3 part mixtures:

| | % w/w |
|---|---|
| A. Topical BRL-34915 gel 0.5% | |
| Part I | |
| Purified water USP | q.s. 100 |
| Carbopol 934P | 0.45 |
| Part II | |
| BRL-34915 | 0.5 |
| Propylene glycol USP | 10 |
| Alcohol USP | 13 |
| Diisopropanolamine NF | 0.45 |
| Part III | |
| Alcohol USP | 27 |
| B. Topical BRL-34915 gel 1.5% | |
| Part I | |
| Purified water USP | q.s. 100 |
| Carbopol 934P | 0.5 |
| Part II | |
| Propylene glycol USP | 20 |
| Alcohol USP | 13 |
| BRL-34915 | 1.5 |
| Diisopropanolamine NF | 0.5 |
| Part III | |
| Alcohol USP | 27 |
| C. Topical BRL-34915 gel 3% | |
| Part I | |
| Purfied water USP | q.s. 100 |
| Carbopol 934P | 0.5 |
| Part II | |
| BRL-34915 | 3.0 |
| Propylene glycol USP | 30 |
| Alcohol USP | 13 |
| Diisopropanolamine NF | 0.5 |
| Part III | |
| Alcohol USP | 27 |

In each of the above cases, the component parts are prepared separately. Parts I and III are each mixed in a Nauta Mixer under vacuum. Part III is then mixed with Part I. When a uniform mixture obtained, Part II is then added using planetary mixing under vacuum until a uniform gel is obtained.

Following the procedure of the preceding Examples 1 and 2, inclusive, compositions are similarly prepared substituting an equimolar amount of another compound within the scope of Formula I for BRL-34915.

Following the procedure of the preceding Examples 1 and 2, inclusive, compositions are similarly prepared substituting an equimolar amount of trans-4-N-acetyl-ethylamino-6-cyano-3,4-dihydro-2,2-dimethyl-2H-benzo[b]pyran-3-ol (the compound of example 1 of U.S. Pat. 4,481,214) for BRL-34915.

Thus, it is intended that modifications and variations of the present invention, which have been hereinbefore disclosed or suggested, be included within the scope of the appended claims except insofar as limited by the prior art.

FORMULA

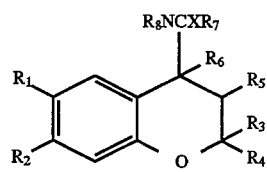

(I)

FORMULA
-continued

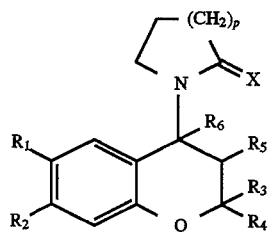

We claim:
1. A method of treating humans for androgenic alopecia which comprises topically applying to the human scalp an effective amount of a pharmaceutical composition containing a compound of Formula I

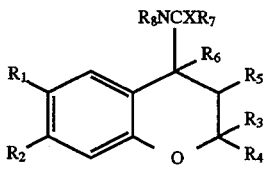

wherein;
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxythiocarbonyl, $C_{1-6}$ alkylthiocarbonyloxy, $C_{1-6}$ alkoxythiolmethyl, formyl or aminosulphinyl, aminosulphonyl or aminocarbonyl, the amino moiety being unsubstituted or substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or
—C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino unsubstituted or substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen hydroxy, $C_{1-6}$ alkoxy or $C_{1-7}$ acyloxy and $R_6$ is hydrogen or $R_5$ and $R_6$ together are a bond;
$R_7$ is
hydrogen,
$C_{1-6}$ alkyl,
$C_{1-6}$ alkyl being substituted by hydroxy,
$C_{1-6}$ alkoxy,
$C_{1-6}$ alkoxycarbonyl or carboxy,
$C_{1-6}$ alkyl substituted by halogen,
$C_{2-6}$ alkenyl,
phenyl,
phenyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups,
naphthyl,
naphthyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$alkyl groups, or
a heteroaryl moiety selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;
$R_8$ is hydrogen or $C_{1-6}$ alkyl; or
$R_7$ and $R_8$ are joined together to form $C_{3-5}$ polymethylene or —CH$_2$—(CH$_2$)$_n$—Z—(CH$_2$)m— where m and n are intergers 0 to 2 such that m+n is 1 or 2 and Z is oxygen, sulphur or NR$_9$ wherein R$_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl unsubstituted or substituted in the phenyl or naphthyl ring by one or two $C_{1-6}$ alkyl, $C_{1-6}$ alkoxy or halogen; mono- or bi-cyclic heteroarylcarbonyl selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;
X is oxygen or sulphur; and the $R_8$NCXR$_7$ moiety is trans to the $R_5$ group when $R_5$ is hydroxy, $C_{1-6}$ alkoxy or $C_{1-7}$ acyloxy; or a pharmaceutically acceptable salt or solvate thereof.

2. The method as defined in claim 1 wherein the compound of Formula I is 6-cyan-3,4-dihydro-2,2-dimethyl-trans-4-(2-oxo-1-pyrrolidinyl)-2H-benzo[b]pyran-3-ol.

3. The method as defined in claim 1 wherein the compound of Formula I is trans-4-N-acetyl-ethylamino-6-cyano-3,4-dihydro-2,2-dimethyl-2H-benzo[b]pyran-3-ol.

4. The method as defined in claim 1 wherein the compound of Formula I is present in the composition in an amount of from about 0.005% to about 10%.

5. The method as defined in claim 2 wherein the compound is present in the composition in an amount of from about 0.05% to about 3.0%.

6. The method as defined in claim 3 wherein the compound is present in the composition in an amount of from about 0.05% to about 3.0%.

7. The method of arresting and reversing male pattern alopecia which comprises continued periodical topical application to the human scalp of a physiologically effective dose of a compound of Formula I

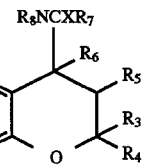

wherein;
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxythiocarbonyl, $C_{1-6}$ alkylthiocarbonyloxy, $C_{1-6}$ alkoxythiolmethyl, formyl or aminosulphinyl, aminosulphonyl or aminocarbonyl, the amino moiety being unsubstituted or substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or $-C(C_{1-6}$ alkyl)NOH or $-C(C_{1-6}$ alkyl)NNH$_2$, or one of $R_1$ and $R_2$ is nitro, cyano or $C_1$-alkylcarbonyl and the other is methoxy or amino unsubstituted or substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is
  hydrogen,
  $C_{1-6}$ alkyl,
  $C_{1-6}$ alkyl being substituted by hydroxy,
  $C_{1-6}$ alkoxy,
  $C_{1-6}$ alkoxycarbonyl or carboxy,
  $C_{1-6}$ alkyl substituted by halogen,
  $C_{2-6}$ alkenyl,
  phenyl,
  phenyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups,
  naphthyl,
  naphthyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups, or
  a heteroaryl moiety selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;

$R_8$ is hydrogen or $C_{1-6}$ alkyl; or $R_7$ and $R_8$ are joined together to form $C_{3-5}$ polymethylene or $-CH_2-(CH_2)_n-Z-(CH_2)m-$ where m and n are intergers 0 to 2 such that m+n is 1 or 2 and Z is oxygen, sulphur or $NR_9$ wherein $R_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl unsubstituted or substituted in the phenyl or naphthyl ring by one or two $C_{1-6}$ alkyl, $C_{1-6}$ alkoxy or halogen; or a mono- or bi-cyclic heteroarylcarbonyl selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;

X is oxygen or sulphur; and the $R_8NCXR_7$ moiety is trans to the $R_5$ group when $R_5$ is hydroxy, $C_{1-6}$ alkoxy or $C_{1-7}$ acyloxy; or a pharmaceutically acceptable salt or solvate thereof;

in association with a topical pharmaceutical carrier.

8. The method as defined in claim 7 wherein the compound of Formula I is 6-cyano-3,4-dihydro-2,2-dimethyl-trans-4-(2-oxo-1-pyrrolidinyl)-2H-benzo[b]pyran-3-ol.

9. The method as defined in claim 7 wherein the compound of Formula I is trans-4-N-ethjylamino-6-cyano-3,4-dihydro-2,2-dimethyl2H-benzo[b]pyran3-ol.

10. The method as defined in claim 8 wherein the compound of Formula I is present in the composition in an amount of from about 0.005% to about 10%.

11. The method as defined in claim 9 wherein the compound of Formula I is present in the composition in an amount of from about 0.005% to about 10%.

12. A topical pharmaceutical solution for the treatment of alopecia consisting of a compound of Formula I

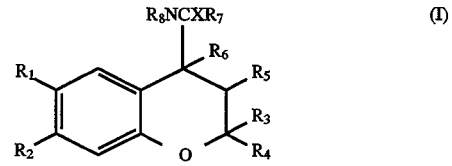

wherein;
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxythiocarbonyl, $C_{1-6}$ alkylthiocarbonyloxy, $C_{1-6}$ alkoxythiolmethyl, formyl or aminosulphinyl, aminosulphonyl or aminocarbonyl, the amino moiety being unsubstituted or substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or $-C(C_{1-6}$ alkyl)NOH or $-C(C_{1-6}$ alkyl)NNH$_2$, or one of $R_1$ and $R_2$ is nitro, cyano or $C_{1-3}$ alkylcarbonyl and the other is methoxy or amino unsubstituted or substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{2-5}$ acyloxy and $R_6$ is hydrogen or $R_5$ and $R_6$ together are a bond;

$R_7$ is hydrogen, $C_{1-6}$ alkyl being unsubstituted or substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl, phenyl or naphthyl either being unsubstituted or substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups and wherein the heteroaryl moiety is selected from the list of groups as defined hereinafter;

$R_8$ is hydrogen or $C_{1-6}$ alkyl; or $R_7$ and $R_8$ are joined together to form $C_{3-5}$ polymethylene or $-CH_2-(CH_2)_n-Z-(CH_2)m-$ where m and n are intergers 0 to 2 such that m+n is 1 or 2 and Z is oxygen, sulphur or $NR_9$ wherein $R_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl unsubstituted or substituted in the phenyl or naphthyl ring by one or two $C_{1-6}$ alkyl, $C_{1-6}$ alkoxy or halogen; mono- or bi-cyclic heteroarylcarbonyl;

and wherein heteroaryl moieties in $R_7$ and $R_9$ are selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;

X is oxygen or sulphur; and the $R_8NCXR_7$ moiety is trans to the $R_5$ group when $R_5$ is hydroxy, $C_{1-6}$ alkoxy or $C_{1-7}$ acyloxy; or a pharmaceutically acceptable salt or solvate thereof;

in association with a vehicle which adapts said solution for topical application to the human skin.

13. A topical pharmaceutical composition consisting of a compound of Formula I

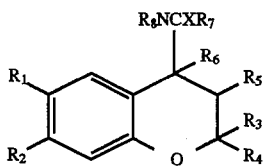

wherein;

either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxythiocarbonyl, $C_{1-6}$ alkylthiocarbonyloxy, $C_{1-6}$ alkoxythiolmethyl, formyl or aminosulphinyl, aminosulphonyl or aminocarbonyl, the amino moiety being unsubstituted or substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino unsubstituted or substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is
hydrogen,
$C_{1-6}$ alkyl,
$C_{1-6}$ alkyl being substituted by hydroxy,
$C_{1-6}$ alkoxy,
$C_{1-6}$ alkoxycarbonyl or carboxy,
$C_{1-6}$ alkyl substituted by halogen,
$C_{2-6}$ alkenyl,
phenyl,
phenyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups,
naphthyl,
naphthyl being substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl being unsubstituted or substituted by one or two $C_{1-6}$ alkyl groups, and
a heteroaryl moiety selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;

$R_8$ is hydrogen or $C_{1-6}$ alkyl; or $R_7$ and $R_8$ are joined together to form $C_{3-5}$ polymethylene or —CH$_2$—(CH$_2$)$_n$—Z—(CH$_2$)m— where m and n are intergers 0 to 2 such that m+n is 1 or 2 and Z is oxygen, sulphur or NR$_9$ wherein R$_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl unsubstituted or substituted in the phenyl or naphthyl ring by one or two $C_{1-6}$ alkyl, $C_{1-6}$ alkoxy or halogen; mono- or bi-cyclic heteroarylcarbonyl selected from the group consisting of furanyl, thienyl, pyrryl, oxazolyl, thiazolyl, imidazolyl, thiadiazolyl, pyridinyl, pyridazinyl, pyrimidinyl, pyrazinyl, thiazinyl, benzofuranyl, benzothiophenyl, indolyl, indazolyl, quinolinyl, isoquinolinyl and quinazoninly;

X is oxygen or sulphur; and the $R_8NCXR_7$ moiety is trans to the $R_5$ group when $R_5$ is hydroxy, $C_{1-6}$ alkoxy or $C_{1-7}$ acyloxy; or a pharmaceutically acceptable salt or solvate thereof;

in association with a topical pharmaceutical carder selected from the group consisting of ointments, lotions, pastes, jellies, gels, mousses, sprays, and aerosols.

* * * * *